United States Patent [19]

Fischell et al.

[11] Patent Number: 5,722,984
[45] Date of Patent: Mar. 3, 1998

[54] ANTITHROMBOGENIC RADIOACTIVE COATING FOR AN INTRAVASCULAR STENT

[75] Inventors: David R. Fischell, Fair Haven, N.J.; Tim A. Fischell, Nashville, Tenn.

[73] Assignee: Iso Stent, Inc., Belmont, Calif.

[21] Appl. No.: 585,760

[22] Filed: Jan. 16, 1996

[51] Int. Cl.$^6$ .............................. A61B 17/00; A61N 5/00
[52] U.S. Cl. .............................................. 606/198; 600/3
[58] Field of Search ................... 606/1, 108, 191–198, 606/200; 600/3, 12; 128/898, 899

[56] References Cited

U.S. PATENT DOCUMENTS 5,059,166  10/1991  Fischell et al. .................. 606/108
5,302,168   4/1994  Hess ..................................... 606/3

Primary Examiner—Michael Buiz
Assistant Examiner—William W. Lewis

[57] ABSTRACT

Disclosed is a coating material which has both antithrombogenic properties and contains an embedded radioisotope that makes the coating material radioactive As phosphorous 32 is emerging as the preferred isotope for vascular radioisotope stents, and phosphorylcholine has shown promise as an antithrombogenic stent coating, it is envisioned here to produce a stent with a phosphorylcholine coating with some of the phosphorous in the coating being phosphorous 32 rather than the naturally occurring, non-radioactive element phosphorous 31. In this manner one has a stent which has a single stent coating which is both antithrombogenic and radioactive. The stent could also utilize an inner layer which is both antithrombogenic and radioactive and an outer layer which is only antithrombogenic. A preferred embodiment of the invention is to produce a phosphorylcholine coated stent where some of the phosphate groups contain the radioisotope phosphorous 32.

2 Claims, 1 Drawing Sheet

ANTITHROMBOGENIC RADIOACTIVE COATING FOR AN INTRAVASCULAR STENT

FIELD OF USE

This invention is in the field of intravascular stents that are used to maintain patency of a blood vessel.

BACKGROUND OF THE INVENTION

It has been shown that endovascular radiation can reduce the proliferation of cells into the lumen of a stent following implant. It has also been shown that an antithrombogenic coating can reduce the incidence of acute and subacute stent thrombosis. Phosphorylcholine stent coatings have recently shown excellent antithrombogenic properties in-vivo. Robert and Tim Fischell in U.S. Pat. No. 5,059,166 (which is included herein by reference) describe a stent that incorporates a radioisotope in or on the metal stent structure. They envision a radioactive coating such as gold 198 plated onto a metal stent wire which in turn could be coated with an antithrombogenic coating. The sequential coating of two different materials on a structure which must expand outward during delivery can be more difficult to accomplish as compared to a single coating that is both radioactive and antithrombogenic.

SUMMARY OF THE INVENTION

This invention utilizes a single coating material which has antithrombogenic properties and contains an embedded radioisotope so as to simplify the process of coating the stent. It is also envisioned that an inner layer with radioisotope and an outer layer without the radioisotope could be sequentially applied and would adhere well as they are essentially the same material. As phosphorous 32 is emerging as the preferred isotope for vascular radioisotope stents, and phosphorylcholine has shown promise as an antithrombogenic stent coating, it is envisioned here to produce a stent with a phosphorylcholine coating with some of the phosphorous in the coating being phosphorous 32 rather than the naturally occurring, non-radioactive element phosphorous 31.

Thus it is an object of the invention to have a single stent coating which is both antithrombogenic and radioactive.

Another object of the invention is to use an inner layer which is both antithrombogenic and radioactive and an outer layer which is only antithrombogenic.

Still another object of the invention is to produce a phosphorylcholine coated stent where some of the phosphate groups contain the radioisotope phosphorous 32.

These and other objects and advantages of this invention will become obvious to a person of ordinary skill in this art upon reading of the detailed description of this invention including associated drawings.

DETAILED DESCRIPTION OF THE DRAWINGS

As described in U.S. Pat. No. 4,768,507, intra-arterial stents can be made in the form of a deployable helical coil spring. FIGS. 5 and 6 of the U.S. Pat. No. 4,768,507 illustrate typical cross sections of such a spring wire, helical coil stent.

Figure 1:
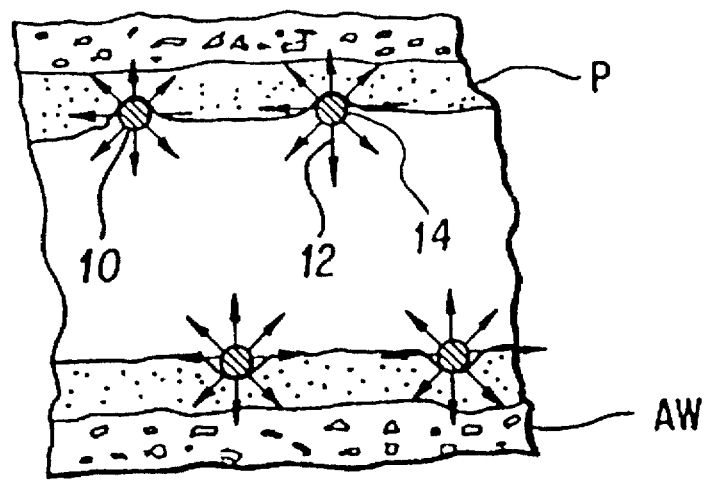
FIG. 1 is a cross section showing two turns of a radioisotope helical coil spring stent imbedded into a balloon dilated or atherectomized plaque within a human artery.
Figure 2:
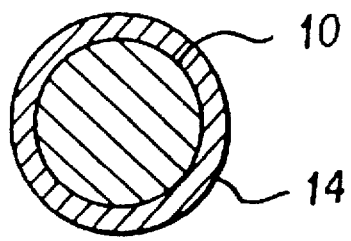
FIG. 2 is a cross section through the stent wire showing a coating which is a combination antithrombogenic and radioactive coating.

FIGS. 1 and 2 of the present invention show a cross sections of two turns of a helical coil spring stent that has been fabricated from metal stem wires 10 which have been coated with an antithrombogenic and radioactive coating 14. These two turns are shown imbedded into plaque P within the arterial wall AW. The arrows 12 pointing outward from the stent wires 10 indicate the omnidirectional emission of radiation from the stent wires 10. The radioisotope used for this purpose may be an alpha, beta or gamma emitter. The half-life would ideally be between 10 hours and 100 days. An optimum emitter might be a beta emitting isotope such as phosphorous 32, with a 14.3 day half-life and no gamma rays.

FIG. 2 shows a cross section of the present invention in which the single layer of antithrombogenic coating 14 which contains a radioisotope is coated onto the stent wire 10.

An example of such a coating is the organic compound phosphorylcholine with at least some portion of the phosphate groups in the organic compound containing the radioisotope phosphorous 32 while the remaining phosphate groups have the natural element phosphorous 31 which is not radioactive.

Another way to produce an antithrombogenic radioactive coating would be to coat the stent wire with a plastic such as polyethylene or Paralene to which heparin molecules can be ionically or covalently bonded. The plastic could include a radioisotope substance such as phosphorous 32.

Figure 3:
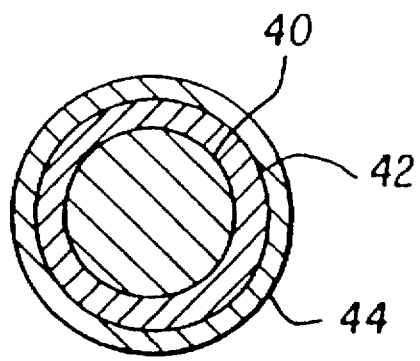
FIG. 3 is a cross section through the stent wire showing two layers of antithrombogenic coating, the inner layer being also radioactive.

FIG. 3 shows an alternate embodiment of the present invention in which two layers of antithrombogenic coating are applied to the stent wire 40. The inner layer 42 contains a radioisotope and the outer layer 44 is not radioactive but is antithrombogenic.

It is also envisioned that the coatings described herein could be applied to intravascular catheters for temporary irradiation of a section of a blood vessel.

Various other modifications, adaptations, and alternative designs are of course possible in light of the above teachings. Therefore, it should be understood at this time that within the scope of the appended claims the invention may be practiced otherwise than as specifically described herein.

What is claimed is:

1. An intravascular stent comprising: a thin, wire-like, generally cylindrical metal structure, the stent having a single layered coating of the metal structure which single layered coating is both antithrombogenic and radioactive.

2. The stent of claim 1 wherein the single layered comprising material that includes the molecule phosphorylcholine and at least some of the phosphorous atoms in phosphorylcholine molecule are phosphorous 32.

\* \* \* \* \*